US006616916B1

(12) United States Patent
Karpe et al.

(10) Patent No.: US 6,616,916 B1
(45) Date of Patent: Sep. 9, 2003

(54) TRANSPARENT DENTIFRICES

(75) Inventors: Rajeev B. Karpe, Mumbai (IN); Sunil S. Nadkarni, Gujarat (IN); Ramanathan Ramakrishnan, Gujarat (IN); John A. Kostinko, Bel Air, MD (US)

(73) Assignee: J. M. Huber Corporation, Edison, NJ (US)

( * ) Notice: Subject to any disclaimer, the term of this patent is extended or adjusted under 35 U.S.C. 154(b) by 0 days.

(21) Appl. No.: 10/016,550

(22) Filed: Dec. 10, 2001

(51) Int. Cl.[7] ............................................... A61K 7/16
(52) U.S. Cl. ........................................ 424/49; 423/339
(58) Field of Search ............... 424/49–58; 423/335–339

(56) References Cited

U.S. PATENT DOCUMENTS

| 3,893,840 A | 7/1975 | Wason |
| 3,988,162 A | 10/1976 | Wason |
| 4,015,996 A | 4/1977 | Wason |
| 4,122,160 A | 10/1978 | Wason |
| 4,144,321 A | 3/1979 | Wason |
| 4,340,583 A | 7/1982 | Wason |
| 4,420,312 A | 12/1983 | Wason |
| 4,421,527 A | 12/1983 | Wason |
| 4,992,251 A * | 2/1991 | Alocroft et al. ............ 423/335 |
| 5,035,879 A * | 7/1991 | Alocroft et al. .............. 424/49 |
| 5,098,695 A * | 3/1992 | Newton et al. ............... 424/49 |
| 5,252,313 A * | 10/1993 | Collins et al. ................ 424/49 |
| 5,279,815 A * | 1/1994 | Wason et al. ................. 424/52 |
| 5,354,550 A * | 10/1994 | Collins et al. ................ 424/49 |
| 5,512,271 A * | 4/1996 | McKeown et al. ........... 424/49 |
| 5,582,816 A * | 12/1996 | Mandanas et al. ............ 424/49 |
| 5,624,652 A | 4/1997 | Aldcroft et al. |
| 5,676,932 A * | 10/1997 | Wason et al. ................. 424/49 |
| 5,932,191 A * | 8/1999 | Chevallier et al. .......... 423/335 |
| 5,964,937 A * | 10/1999 | Stanier ....................... 423/339 |
| 6,171,384 B1 | 1/2001 | Conley et al. |
| 6,290,933 B1 * | 9/2001 | Durga et al. .................. 424/49 |
| 6,294,155 B1 * | 9/2001 | Thomas et al. ............... 424/49 |
| 6,399,111 B1 * | 6/2002 | Stanier ........................ 424/49 |
| 6,403,059 B1 * | 6/2002 | Martin et al. ................. 424/49 |
| 6,419,174 B1 * | 7/2002 | McGill et al. .............. 423/335 |

* cited by examiner

*Primary Examiner*—Shep Rose
(74) *Attorney, Agent, or Firm*—Carlos Nieves; D. Mitchell Goodrich

(57) ABSTRACT

An abrasive, amorphous precipitated silica is provided that provides excellent abrasive performance, but also has a relatively high degree of transmittance, and an index of refraction that is sufficiently low to allow it to be a component of a transparent toothpaste composition having a relatively high concentration of water. The amorphous precipitated silica composition has a refractive index of less than about 1.4387, a light transmittance of greater than about 48%; and a Brass Einlehner abrasion value of greater than about 5 mg loss/100,000 rev. A dentifrice having a haze value of less than about 70 may be prepared using this abrasive, amorphous silica.

6 Claims, 1 Drawing Sheet

TRANSPARENT DENTIFRICES

BACKGROUND OF THE INVENTION

Precipitated silicas find use in a broad range of manufactured products ranging from cosmetic and food products to industrial coatings and elastomeric materials, such as tires. Silicas are particularly useful in dentifrice products (such as toothpastes) where they function as fillers, abrasives, and thickeners. Because of this functional versatility, and also because silicas have a relatively high compatibility with active ingredients like fluoride compared to other dentifrice abrasive (notably alumina and calcium carbonate), there is a strong desire among toothpaste and dentifrice formulators to include them in their products.

However, it can be difficult to incorporate abrasive silicas into transparent dentifrice products, which have become increasingly popular in recent years because of their greater appeal to some consumers and because they allow manufacturers to impart increased distinctiveness to their product. This formulation difficulty arises because in order to produce a silica-containing transparent toothpaste, it is necessary to ensure that the refractive index of the silica closely matches the refractive index of the toothpaste matrix, that the silica has a high degree of light transmittance, and that the silica has sufficient abrasivity to provide cleaning of the tooth surfaces, when incorporated into a dentifrice.

The requirement that the refractive index of the silica match the refractive index of the toothpaste generally means that the concentration of water in the toothpaste must be maintained at relatively low levels. Water generally has a far lower refractive index than silica (commercially available silicas have a refractive index of 1.438 to 1.451, while water has a refractive index of 1.332), and so as the toothpaste's water concentration increases, the refractive index of the toothpaste decreases. Accordingly, in order for the refractive index of the silica to match the refractive index of the toothpaste, the water concentration in the toothpaste must be minimized. This is undesirable because water is generally the least expensive component of a toothpaste, and decreases in water concentration are normally offset by increases in humetctant concentration (which is quite expensive). Thus, decreasing water concentration will cause a corresponding increasing in the toothpaste unit cost.

Thus, a toothpaste formulator striving to produce a transparent gel toothpaste must balance several factors. Silica is an indispensable ingredient to produce a toothpaste that is effective at cleaning teeth, but adding silica can reduce the transparency of the overall toothpaste product because of its low degree of transmittance and high refractive index. So while adding silica provides cleaning benefits, the silica's high refractive index requires a decrease in the water concentration and a concomitant increase in the humetctant concentration, resulting in a significant increase in product cost.

Given the foregoing, there is a continuing need for a silica composition that not only provides excellent abrasive performance, but also has a relatively high degree of transmittance, and an index of refraction that is sufficiently low, such that the silica can be included in a transparent toothpaste composition having a relatively high concentration of water.

BRIEF SUMMARY OF THE INVENTION

The invention includes an amorphous precipitated silica composition, the silica composition having a refractive index of less than about 1.4387, a light transmittance of greater than about 48%; and a Brass Einlehner abrasion value of greater than about 5 mg loss/100,000 rev.

The invention also includes a dentifrice comprising a premix containing no silica, wherein the premix has a refractive index of less than 1.442. The dentifrice also comprises about 0.01 wt % to about 10 wt % of an abrasive silica, and has a RDA of greater than about 50.

The invention also includes a method of preparing a dentifrice comprising the steps of preparing a premix, which contains no silica and has a refractive index of less than about 1.442, and mixing silica with the premix to form a dentifrice having an RDA of greater than about 50.

BRIEF DESCRIPTION OF THE DRAWING

The foregoing summary, as well as the following detailed description of preferred embodiments of the invention, will be better understood when read in conjunction with the appended drawing. It should be understood, however, that the invention is not limited to the precise physical relationships shown in the drawings.

DETAILED DESCRIPTION OF THE INVENTION

Figure 1:
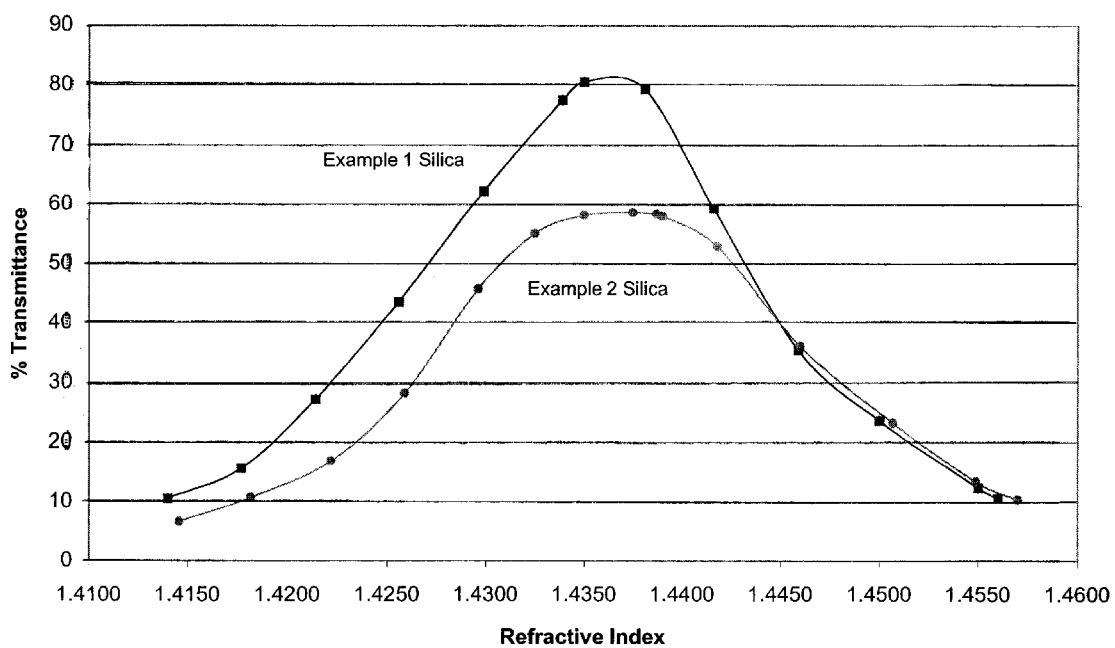
FIG. 1 is a curve that plots the relationship between the degree of light transmittance ("Transmittance") versus the refractive index for precipitated silica prepared according to the present invention.

All parts, percentages and ratios used herein are expressed by weight unless otherwise specified. All documents cited herein are incorporated by reference. The following describes preferred embodiments of the present invention, which provides silica for use in dentifrices, such as toothpastes. While the optimal use for this silica is in dentifrices, this silica may also be used in a variety of other consumer products By "mixture" it is meant any combination of two or more substances, in the form of, for example without intending to be limiting, a heterogeneous mixture, a suspension, a solution, a sol, a gel, a dispersion, or an emulsion.

By "transparent", it is meant transmitting light so that images can be seen as if there were no intervening material.

By "dentifrices" it is meant oral care products such as, without intending to be limiting, toothpastes, tooth powders and denture creams.

By "low-structure silica" it is meant that the silica material has an oil absorption of between about 70 ml/100 g and 90 ml/100 g.

The present invention relates to amorphous, low-structure precipitated silica compositions, also known as silicon dioxide, or $SiO_2$, which impart improved cleaning and abrasive characteristics when included within a toothpaste or dentifrice. These abrasive silicas not only clean teeth by removing debris and residual stains, but also function to polish tooth surfaces. Because they have a lower refractive index than most comparable commercially-available amorphous silicas, and also because of their high degree of light transmittance, the silicas of the present invention are particularly useful for formulating a low-cost, transparent toothpaste that has a relatively high concentration of water.

A sufficient amount of abrasive silica should be added to a toothpaste composition so that the radioactive dentin abrasion ("RDA") value of the toothpaste is between about 50 and 200. At a RDA of less than 50, the cleaning benefits of the toothpaste will be minimal, while at a RDA of greater than 200, there is serious risk that the toothpaste will be so abrasive that it may damage the tooth dentin along the gum line. Most commercial toothpaste products today have a RDA in the range of 50 to 150, with the average being exactly in the middle around 100. Preferably, the dentifrice should have a RDA value of at least about 50, such as between 70 and 120, such as between 90 and 110.

The RDA of a toothpaste is dependent on both the hardness (abrasiveness) of the abrasive and the concentration of the abrasive in the toothpaste. The RDA is measured by the method described in the article "A Laboratory Method for Assessment of Dentifrice Abrasivity", John J. Hefferren, in *Journal of Dental Research*, Vol. 55, no. 4 (1976), pp. 563–573. Silica abrasivity can be measured by an Einlehner method, which is described in greater detail below. A correlation between silica Einlehner values, silica loading level in toothpaste and RDA values has been determined from historical data, and is summarized in equation (I) below:

$$RDA=(0.099003 \times E)+(0.773864 \times L)+(0.994414 \times E \times L)+(-0.002875 E^2)+(-0.094783 \times L^2)+(3.417937) \quad (I)$$

where E is the brass Einlehner mg lost for an aqueous 10% silica slurry

L is the weight % silica loading in the toothpaste

For example, if a toothpaste contains 20 wt % of a silica having an Einlehner abrasion value (a measure of hardness, described in greater detail below) of about 6.0, then the toothpaste will have a RDA of about 100. A toothpaste having the same RDA value of about 100 could be obtained at a silica concentration level of about 6.5 wt % with a more abrasive silica, such as a silica having an Einlehner abrasion value of 15. Including this same silica having an Einlehnher abrasion value of 15 at a 20 wt % concentration level would produce a toothpaste having a RDA of about 280.

Because these two silicas having different abrasive values are commensurate in cost, it is more cost-effective to use the more abrasive silicas at lower concentrations. Unfortunately, while low abrasive silicas (e.g., the silicas having Einlehner values of about 4.0) generally have good transparency properties (viz., high refractive index and a high degree of light transmittance), the more abrasive silicas were generally poor candidates for inclusion in a transparent dentifrice.

However, by the present invention, abrasive amorphous silicas have been developed that not only have excellent abrasion performance but are also are suitable for inclusion in a transparent toothpaste. By controlling the agitator rpm, the digest time, addition rate, batch (final) pH, and slurry pH, a silica abrasive may be produced that has a relatively low refractive index, a high degree of light transmittance, and is sufficiently abrasive.

The silica compositions of the present invention are prepared according to the following process. In this process, an aqueous solution of an alkali silicate, such as sodium silicate, is charged into a reactor, such as a reactor equipped with mixing means adequate to ensure a homogeneous mixture, and the aqueous solution of an alkali silicate in the reactor preheated to a temperature of between about 65° C. and about 100° C. Preferably, the alkali silicate aqueous solution has an alkali silicate concentration of approximately 8.0 to 35 wt %, such as from about 8.0 to about 15 wt %. Preferably the alkali silicate is a sodium silicate with a $SiO_2:Na_2O$ ratio of from about 1 to about 3.5, such as about 2.5 to about 3.4.

To the reactor is then simultaneously added: (1) an aqueous solution of acidulating agent or acid, such as sulfuric acid, and (2) additional amounts of an aqueous solution containing the same species of alkali silicate as is in the reactor, the aqueous solution being preheated to a temperature of about 65° C. to about 85° C. The aqueous acidulating agent solution preferably has a concentration of acidulating agent of about 6 to 35 wt %, such as about 9.0 to about 15 wt %. The simultaneous addition is continued until the reactor batch pH drops to between about 5.4 to about 6.4.

After the inflows of the acidulating agent and the alkali silicate are stopped, the reactor batch is heated to a temperature of between about 85° C. and 100° C., and the reactor batch allowed to age or "digest" for between 5 minutes to 60 minutes, with the reactor batch being maintained at a constant pH. After the completion of digestion, the reaction batch is filtered and washed with water to remove excess inorganic salts until the wash water from the silica filter cake obtains a conductivity of less than about 2000 $\mu$mhos. Because the conductivity of the silica filtrate is proportional to the inorganic salt by-product concentration in the filter cake, then by maintaining the conductivity of the filtrate to be less than 2000 $\mu$mhos, the desired low concentration of inorganic salts, such as $Na_2SO_4$, in the filter cake may be obtained.

The silica filter cake is slurried in water, and then dried by any conventional drying techniques, such as spray drying, to produce a precipitated silica containing from about 3 wt % to about 50 wt % of moisture. The precipitated silica may then be milled to obtain the desired particle size of between about 5 $\mu$m to 25 $\mu$m, such as about 5 $\mu$m to about 15 $\mu$m.

This abrasive, amorphous precipitated silica may then be incorporated into a dentifrice composition, e.g., a toothpaste.

In addition to the abrasive component, the dentifrice may also contain several other ingredients such as humectants, thickening agents, (also sometimes known as binders, gums, or stabilizing agents), antibacterial agents, fluorides, sweeteners, and cosurfactants.

Humectants serve to add body or "mouth texture" to a dentifrice as well as preventing the dentifrice from drying out. Suitable humectants include polyethylene glycol (at a variety of different molecular weights), propylene glycol, glycerin (glycerol), erythritol, xylitol, sorbitol, mannitol, lactitol, and hydrogenated starch hydrolyzates, as well as mixtures of these compounds.

Thickening agents are useful in the dentifrice compositions of the present invention to provide a gelatinous structure that stabilizes the toothpaste against phase separation. Suitable thickening agents include silica thickener, starch, glycerite of starch, gum karaya (sterculia gum), gum tragacanth, gum arabic, gum ghatti, gum acacia, xanthan gum, guar gum, veegum, carrageenan, sodium alginate, agar-agar, pectin, gelatin, cellulose, cellulose gum, carboxymethyl cellulose, hydroxyethyl cellulose, hydroxypropyl cellulose, hydroxymethyl, hydroxymethyl carboxypropyl cellulose, methyl cellulose, ethyl cellulose, sulfated cellulose, as well as mixtures of these compounds. Typical levels of binders are from about 0 wt % to about 15 wt % of a toothpaste composition.

Antibacterial agents may be included to reduce the presence of microorganisms to below known harmful levels. Suitable antibacterial agents include benzoic acid, sodium benzoate, potassium benzoate boric acid phenolic compounds such as betanapthol, chlorothymol, thymol, anethole, eucalyptol, carvacrol, menthol, phenol, amylphenol, hexylphenol, heptylphenol, octylphenol, hexylresorcinol, laurylpyridinium chloride, myristylpyridinium chloride, cetylpyridinium fluoride, cetylpyridinium chloride, cetylpyridinium bromide. If present, the level of antibacterial agent is preferably from about 0.1 wt % to about 5 wt % of the toothpaste composition.

Sweeteners may be added to the toothpaste composition to impart a pleasing taste to the product. Suitable sweeteners include saccharin (as sodium, potassium or calcium saccharin), cyclamate (as a sodium, potassium or calcium salt), acesulfane-K, thaumatin, neohisperidin dihydrochalcone, ammoniated glycyrrhizin, dextrose, levulose, sucrose, mannose, and glucose.

The toothpaste will also preferably contain fluoride salts to prevent the development and progression of dental caries. Suitable fluoride salts include sodium fluoride, potassium fluoride, calcium fluoride, zinc fluoride, stannous fluoride, zinc ammonium fluoride, sodium monofluorophosphate, potassium monofluorophosphate, laurylamine hydrofluoride, diethylaminoethyloctoylamide hydrofluoride, didecyldimethylammonium fluoride, cetylpyridinium fluoride, dilaurylmorpholinium fluoride, sarcosine stannous fluoride, glycine potassium fluoride, glycine hydrofluoride, and sodium monofluorophosphate. Typical levels of fluoride salts are from about 0.1 wt % to about 5 wt %.

Surfactants may also be included as additional cleansing and foaming agents, and may be selected from anionic surfactants, zwitterionic surfactants, nonionic surfactants, amphoteric surfactants, and cationic surfactants. Anionic surfactants are preferred, such as metal sulfate salts, such as sodium lauryl sulfate.

The dentifrices disclosed herein may also a variety of additional ingredients such as desensitizing agents, healing agents, other caries preventative agents, chelating/sequestering agents, vitamins, amino acids, proteins, other anti-plaque/anti-calculus agents, opacifiers, antibiotics, anti-enzymes, enzymes, pH control agents, oxidizing agents, antioxidants, whitening agents and preservatives.

Finally, water provides the balance of the composition in addition to the additives mentioned. The water is preferably deionized and free of impurities. The dentifrice will comprise from about 13 wt % to about 20 wt % of water.

The invention will now be described in more detail with respect to the following, specific, non-limiting examples.

EXAMPLES 1–4

In Examples 1–4, silicas suitable for use in dentifrices as well as other products, were prepared according to the present invention. First, 900 kg of an aqueous solution containing 14.36 wt % of sodium silicate (having a 3.3 molar ratio of $SiO_2Na_2O$) was charged into a reactor, heated to 82° C., and maintained at that same temperature during the digestion step, while the reactor was agitated at 83 rpm. An aqueous solution of sulfuric acid (at a concentration of 12.06 wt %) and an aqueous solution of sodium silicate (at a concentration of 14.36 wt %, the sodium silicate having a 3.3 mole ratio, the solution heated to 75° C.) were then added simultaneously at rates of 113 liters/minute and 377 liters/minute, respectively. The silicate addition was stopped after 47 minutes and the acid addition continued until the reactor batch pH dropped to 5.8–6.0. The batch temperature was then maintained at 93° C. for 10 minutes, at the same pH. The silica batch was then filtered and washed to form a filter cake having a conductivity of not more than about 2000 μmhos. The filter cake was then slurried with water, so that the solids content was at 32.4% and the pH adjusted to 7.20. The filter cake was then spray dried at a spray drier inlet temperature of 650° C. and outlet temperature of 78 ° C., and the spray dried product milled to between 8–10 μm.

In Examples 2–3 silicas, suitable for use in dentifrices as well as other products, were prepared according to the present invention. First, 27 L of an aqueous solution containing 14.5 wt % sodium silicate (having a 3.3 mole ratio) was charged into a 400-gallon reactor, equipped with an A-200 pitched four blade (45 degree) turbine impeller, heated to 82° C., and maintained at this temperature until the digestion step. The reactor contents were agitated at the speeds indicated in Table I, below. An aqueous solution comprising 12.4 wt % sulfuric acid, and an aqueous solution comprising 14.5 wt % sodium silicate (having a 3.3 mole ratio and heated to 75 ° C.) are added then simultaneously at the rates given in Table I, below. The silicate addition was stopped after 47 minutes and the acid addition continued at the same rate until the batch pH drops to 7.5. The acid addition rate is then reduced to 1.0 to 1.5 liters/minute until the batch pH approaches the final pH. The final batch pH is manually adjusted to target. The batch then enters the digestion step, where the temperature is increased to 93 ° C., while the batch pH is maintained at the final pH throughout the digestion step. The timing of the digestion step in each example is given in Table I below.

After digestion, the silica batch is filtered on a filter press and washed until the filtrate had a conductivity of not more than 2000 μmhos. The filter cake is then slurried with water and mixed for 5 minutes with a Cowles agitator to form a cake slurry having the solids content listed in Table I, below. The pH of the cake slurry may then be further adjusted by the optional addition of caustic soda to arrive at the pH indicated in the "Slurry pH" column in Table I, below. The cake slurry is then spray dried (at the inlet and outlet temperature shown in Table I, below) and milled to form a particulate silica composition having an average particle size of from about 8.7 μm to about 9.7 μm.

COMPARATIVE EXAMPLES 1–2

Comparative Examples 1–2 were prepared using the same method as described above with respect to examples 2–3, but according to the processing parameters set forth in Table I, below.

TABLE I

|  | Agitator rpm | Silicate rate LPM | Acid rate LPM | Digest time, min | Batch Final pH | % Slurry Solids | Slurry pH | Inlet Temp ° C. | Outlet Temp ° C. |
| --- | --- | --- | --- | --- | --- | --- | --- | --- | --- |
| Example 2 | 50 | 12.6 | 3.8 | 10 | 5.8–6.0 | 33.1 | 6.6 | 440 | 76 |
| Example 3 | 50 | 12.6 | 3.8 | 10 | 5.8–6.0 | 36.8 | 6.97 | 390 | 88 |
| Comparative Example 1 | 50 | 12.6 | 3.8 | 10 | 6.5–6.7 | 20.8 | 8.8 | 420 | 76 |
| Comparative Example 2 | 50 | 12.6 | 3.8 | 40 | 5.8–6.0 | 22.7 | 7.1 | 440 | 76 |

After being prepared as set forth above, several properties of the particulate silica, including Einlehner abrasion, oil absorption, silica particle size, refractive index, the degree of light transmission ("% Transmittance"), and brightness were then measured. As a first step in measuring the refractive index ("RI") and degree of light transmission, a range of sorbitol/water stock solutions (about 10) was prepared so that the refractive index of these solutions lies between about 1.426 and 1.440. The exact sorbitol/water ratios needed depend on the exact sorbitol used and is determined by the technician making the measurement. Typically, these stock solutions will cover the range of 49 to 70 wt. % sorbitol in water. To determine Refractive Index, one or two drops of each standard solution is separately placed on the fixed plate of the refractometer (Abbe 60 Refractometer Model 10450). The covering plate is fixed and locked into place. The light source and refractometer are switched on and the refractive index of each standard solution is read. Into separate 20 cm$^3$ bottles, accurately weigh 0.5 g±0.01 silica and add 12.0 g±0.01 of each respective stock sorbitol/water solution. The bottles were then shaken vigorously to form silica dispersions, the stoppers removed from the bottles, and the bottles were placed in a desiccator, which was then evacuated with a vacuum pump.

The dispersions are de-aerated for 30 minutes and visually inspected for complete de-aeration. The %Transmittance ("%T") at 589 nm (Spectronic 20 D±) is immediately measured, according to the manufacturer's operating instructions. Specifically, %Transmittance is measured on the silica/sorbitol/water dispersions by placing an aliquot of each dispersion in a quartz cuvette and reading the %T at 589 nm wavelength for each sample on a 0–100 scale. %Transmittance vs. RI of the stock solutions used is plotted on a curve, as shown in FIG. 1, for Example 1 and Example 3. The Refractive index of the silica is defined as the position (the ordinate or X value) of the plotted peak maximum on the %Transmittance vs. RI curve. The value of Y-axis (the abscissa) of the peak maximum is the %Transmittance of the silica.

The Brass Einlehner (BE) Abrasion value was measured through the use of an Einlehner AT-1000 Abrader. In this test, a Fourdrinier brass wire screen is weighed and exposed to the action of a 10% aqueous silica suspension for a fixed number of revolutions, and the amount of abrasion is then determined as milligrams brass lost from the Fourdrinier wire screen per 100,000 revolutions. Disposable supplies required for this test (brass screens, wear plates and PVC tubing) are available from Duncan Associates, Rutland, Vermont and sold as an "Einlehner Test Kit". Specifically, brass screens (Phosphos Bronze P.M.) were prepared by washing in hot, soapy water (0.5% Alconox) in an ultrasonic bath for 5 minutes, then rinsed in tap water and rinsed again in a beaker containing 150 ml water set in an ultrasonic bath. The screen is rinsed again in tap water, dried in an oven set at 105° C. for 20 minutes, cooled in a desiccator and weighed. Screens were handled with tweezers to prevent skin oils from contaminating the screens. The Einlehner test cylinder is assembled with a wear plate and weighed screen (red line side down—not abraded side) and clamped in place. The wear plate is used for about 25 tests or until worn badly; the weighed screen is used only once.

A 10% silica slurry, prepared by mixing 100 g silica with 900 g deionized water, was poured into the Einlehner test cylinder. Einlehner PVC tubing was placed onto the agitating shaft. The PVC tubing has 5 numbered positions. For each test, the position of the PVC tubing is incremented until it has been used five times, then discarded. The Einlehner abrasion instrument is re-assembled and the instrument set to run for 87,000 revolutions. Each test takes about 49 minutes. After the cycle is completed, the screen is removed rinsed in tap water, placed in a beaker containing water and set in an ultrasonic bath for 2 minutes, rinsed with deionized water and dried in an oven set at 105° C. for 20 minutes. The dried screen is cooled in a desiccator and reweighed. Two tests are run for each sample and the results are averaged and expressed in mg lost per 100,000 revolutions. The result, measured in units of mg lost per 100,000 revolutions, for a 10% slurry can be characterized as the 10% brass Einlehner (BE) abrasion value.

The Mean Particle Size is determined using a Leeds and Northrup Microtrac II. A laser beam is projected through a transparent cell which contains a stream of moving particles suspended in a liquid. Light rays that strike the particles are scattered through angles that are inversely proportional to their sizes. The photodetector array measures the quantity of light at several predetermined angles. Electrical signals proportional to the measured light flux values are then processed by a microcomputer system to form a multichannel histogram of the particle size distribution.

To measure the brightness values, fine powder materials are pressed into a smooth surfaced pellet and are evaluated using a Technidyne Brightmeter S-5/BC. This instrument has a dual beam optical system where the sample is illuminated at an angle of 450, and the reflected light viewed at 0°. It conforms to TAPPI test methods T452 and T646, and ASTM Standard D985. Powdered materials are pressed to about a 1 cm thick pellet with enough pressure to give a pellet surface that is smooth and flat and without loose particles or gloss.

The oil absorption was measured using linseed oil by the rubout method. In this test, oil is mixed with a silica and rubbed with a spatula on a smooth surface until a stiff putty-like paste is formed. By measuring the quantity of oil required to have a paste mixture, which will curl when spread out, one can calculate the oil absorption value of the silica - the value which represents the volume of oil required per unit weight of silica to completely saturate the silica sorptive capacity. Calculation of the oil absorption value was done as follows:

$$\text{Oil absorption} = \frac{\text{ml oil absorbed}}{\text{weight of silica, grams}} \times 100 \quad (II)$$

$$= \text{ml oil}/100 \text{ gram silica}$$

The results of these measurements and tests are given below in Table II.

TABLE II

|  | Einlehner abrasion (mg) | Oil Absorption (ml/100 g) | Refractive Index | % Transmittance | Brightness | Mean Particle Size (μm) |
|---|---|---|---|---|---|---|
| Example 1 | 5.7 | 90 | 1.4343 | 78 | 95.7 | 9.5 |
| Example 2 | 9.7 | 71 | 1.4350 | 63 | 98.1 | 9.0 |
| Example 3 | 7.3 | 75 | 1.4387 | 58 | 97.4 | 9.7 |
| Comparative Example 1 | 13.2 | 75 | 1.4334 | 45 | 96.9 | 9.0 |
| Comparative Example 2 | 18.2 | 71 | 1.4358 | 48 | 97.8 | 9.7 |

As can be seen in table II, the silicas prepared in Examples 1–3 met all the criteria for producing a transparent toothpaste (viz., each had a low index of refraction and high degree of light transmittance) while also being sufficiently hard or abrasive to produce a toothpaste with acceptable or good cleaning performance. By contrast, Comparative Examples 1 and 2 are highly abrasive, as indicated by their high Einlehner abrasion values, have a low refractive index, but also have an undesirably low degree of light transmittance.

To demonstrate their efficacy in consumer products, the silica abrasives of Examples 1–3 were incorporated as powders into four different toothpaste compositions (numbers 1–4), which are set forth in Table III, below. The performance of these compositions was then compared with the performance of the following toothpaste compositions: compositions 5–6, which contain silica abrasives prepared according to comparative examples 1–2; toothpaste composition 7, which contains a prior art silica abrasive (Zeodent® 115 from the J.M. Huber Corporation, Edison, N.J.); and toothpaste composition 8, which contains no silica abrasive. These toothpaste samples were prepared as follows. A first mixture was formed by combining the following components: glycerin and/or sorbitol, polyethylene glycol (CARBOWAX 1450, from the Union Carbide Corporation, Danbury, Conn.), carboxymethylcellulose (CMC-9M31XF, from the Aqualon division of Hercules Corporation, Wilmington, Del.), and then stirring the first mixture until the components dissolved. A second mixture was formed by combining the following components: deionized water, sodium saccharin, sodium fluoride, and then stirring until the components are dissolved. The first and second mixtures were then combined while stirring to form a premix.

The premix was placed into a Ross mixer (model 130LDM, Charles Ross & Co., Haupeauge, N.Y.), silica thickener and silica abrasive added to the premix, and the premix mixed without vacuum. Then 30 inches of vacuum was drawn and each sample mixed for 15 minutes, and then sodium lauryl sulfate and flavor was added. The resulting mixture was stirred for 5 minutes at a reduced mixing speed. The eight different toothpaste compositions were prepared according to the following formulations, wherein the amounts are gram units:

TABLE III

| Ingredients | Composition Number | | | | | | | |
|---|---|---|---|---|---|---|---|---|
|  | 1 | 2 | 3 | 4 | 5 | 6 | 7 | 8 |
| Sorbitol, 70% | 59.707 | 0.00 | 0.00 | 0.00 | 0.00 | 0.00 | 0.00 | 0.00 |
| Glycerin, 99.5% | 0.00 | 59.743 | 60.870 | 59.296 | 59.030 | 60.568 | 47.556 | 58.055 |
| Deionized Water | 19.177 | 19.914 | 20.287 | 19.765 | 19.327 | 20.189 | 15.851 | 19.352 |
| Carbowax 1450 | 4.000 | 4.000 | 4.000 | 4.000 | 4.000 | 4.000 | 4.000 | 4.000 |
| CMC-9M31F | 0.700 | 1.250 | 1.350 | 1.146 | 1.050 | 1.350 | 0.00 | 0.00 |
| Sodium Benzoate | 0.200 | 0.200 | 0.200 | 0.200 | 0.200 | 0.200 | 0.200 | 0.200 |
| Sodium Saccharin | 0.200 | 0.200 | 0.200 | 0.200 | 0.200 | 0.200 | 0.200 | 0.200 |
| Sodium Fluoride | 0.243 | 0.243 | 0.243 | 0.243 | 0.243 | 0.243 | 0.243 | 0.243 |
| Zeodent® 167 silica thickener | 8.000 | 8.000 | 8.500 | 8.000 | 8.000 | 8.000 | 0.00 | 16.000 |
| Example 1 abrasive | 8.000 | 0.00 | 0.00 | 0.00 | 0.00 | 0.00 | 0.00 | 0.00 |
| Example 2 abrasive | 0.00 | 4.500 | 0.00 | 0.00 | 0.00 | 0.00 | 0.00 | 0.00 |
| Example 3 abrasive | 0.00 | 0.00 | 2.400 | 5.200 | 0.00 | 0.00 | 0.00 | 0.00 |
| Comparative Example 1 abrasive | 0.00 | 0.00 | 0.00 | 0.00 | 6.000 | 0.00 | 0.00 | 0.00 |
| Comparative Example 2 abrasive | 0.00 | 0.00 | 0.00 | 0.00 | 0.00 | 3.300 | 0.00 | 0.00 |
| Zeodent® 115 abrasive | 0.00 | 0.00 | 0.00 | 0.00 | 0.00 | 0.00 | 30.000 | 0.00 |
| F&DC Red #2 2.0% | 0.100 | 0.100 | 0.100 | 0.100 | 0.100 | 0.100 | 0.100 | 0.100 |
| Sodium Lauryl Sulfate | 1.200 | 1.200 | 1.200 | 1.200 | 1.200 | 1.200 | 1.200 | 1.200 |
| Flavor | 0.650 | 0.650 | 0.650 | 0.650 | 0.650 | 0.650 | 0.650 | 0.650 |
| Total | 100 | 100 | 100 | 100 | 100 | 100 | 100 | 100 |

After toothpaste compositions 1–8 were prepared as above, properties relating to the gel toothpaste clarity, such as refractive index, clarity and haze were determined as follows.

The toohpaste refractive index was measured by taking a drop of toothpaste and placing on an Abbe 60 Refractometer Model 10450, and the refractive index is directly read.

Clarity is a subjective measurement, wherein a bead of toothpaste is squeezed onto a sheet of white paper containing typed text. A score of 10 is given if the text can be read perfectly, a score of 1 when the text cannot be seen and intermediate scores of 2 to 9 for progressively better clarity of the text. A score of 8 or better is deemed a good clear gel toothpaste, indicating the silica abrasive is transparent. Typically, a toothpaste clarity rating of 10 will have a corresponding haze value (described below) of less than 40; clarity rating of 9, a haze value of about 50–60; and a clarity rating of 8, a haze value of about 60–70.

The "haze value" of the clear gel toothpaste is measured by light transmission utilizing a Gardner XL-835 Colorimeter. The instrument is first calibrated according to the manufacturer's directions. Next, two microscope slides, having dimensions of 38×75mm, and a thickness 0.96 to 1.06 mm, are placed on a flat surface. One slide is covered with a plexiglass spacer, (38×75 mm, 3 mm thickness, with 24×47mm open area). The gel toothpaste in squeezed into the open area of the plexiglass spacer. The second slide is placed over the toothpaste and pressure applied, by hand, to eliminate excess toothpaste and air. The sample is placed on the transmission light beam of the pre-calibrated meter and the haze value is recorded from three different specimen locations and averaged. Lower have values described clearer, transparent toothpastes.

The results of the refractive index, clarity, and haze value measurements are set forth in table IV, below.

TABLE IV

|  | 1 | 2 | 3 | 4 | 5 | 6 | 7 | 8 |
|---|---|---|---|---|---|---|---|---|
| Premix Refractive Index | 1.4418 | 1.4408 | 1.4401 | 1.4418 | 1.4409 | 1.4395 | 1.4402 | 1.4400 |
| Toothpaste Refractive Index | 1.4461 | 1.4448 | 1.4441 | 1.4448 | 1.4453 | 1.4423 | 1.4417 | 1.4426 |
| Expected RDA | 50 | 50 | 50 | 100 | 50 | 50 | 100 | 10 |
| Clarity Rating | 10 | 8 | 9 | 8 | 6 | 7 | 1 | 8 |
| Haze | 39 | 64 | 53 | 68 | 74 | 69 | 95 | 71 |

Toothpaste compositions 7 and 8 were control compositions. Toothpaste composition 7 contained a prior art abrasive silica (Zeodent® 1 15), while toothpaste composition 8 contained thickener-silica but no abrasive silica. As can be seen in Table IV Toothpaste composition 7 had excellent abrasive performance, but poor transparency properties, which make it unsuitable for use in a transparent high water toothpaste formulation. These poor transparency properties are due to its high refractive index (1.4510). By contrast, toothpaste composition 8 had good transparency performance, but its lack of abrasive silica caused it to have totally inadequate cleaning performance.

Toothpaste compositions 1–4 contained silicas prepared in Examples 1–3, which were prepared according to the present invention, and (as discussed above) had adequate or good abrasive performance and met all the criteria for producing a transparent toothpaste (viz., each had a low index of refraction and high degree of light transmittance).

As a result toothpaste compositions 1–4 all had excellent transparency characteristics and acceptable or good cleaning performance.

Toothpaste compositions 5–6 contained silicas prepared in comparative examples 1 and 2. These silicas (as discussed above) are highly abrasive, as indicated by their high Einlehner abrasion values, but also have a low degree of light transmittance. As a result, Toothpaste compositions 5–6 had acceptable abrasive performance, but poor transparency.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A transparent dentifrice comprising:
   about 13 wt % to about 20 wt % water;
   an abrasive, precipitated silica having:
      a refractive index of less than about 1.4387;
      a light transmittance of greater than about 48%; and
      a Brass Einlehner abrasion value of greater than about 5 mg loss/100,000 rev.; wherein the dentifrice has:
      a haze value of less than about 70;
      a refractive index of less than about 1.442; and
      an RDA of about 50 to 150.

2. The dentifrice according to claim 1, wherein the dentifrice has a haze value o0less than about 55.

3. A dentifrice comprising:
   a) a premix consisting essentially of a non-silica thickening agent, deionized water, and a humetctant selected form the group consisting of glycerin, sorbitol, and polyethylene glycol; wherein the premix has a refractive index of less than 1.442; and
   b) about 0.01 wt % to about 10 wt % abrasive, precipitated silica, having:
      a refractive index of less than about 1.4387;
      a light transmittance of greater than about 481%; and
      a Brass Einlehner abrasion value of greater than about 5 mg loss/100,000 rev;
      wherein the dentifrice has an RDA of greater than about 50, a refractive index of less than about 1.442; and a haze value of less than about 70.

4. The dentifrice according to claim 3, wherein the dentifrice is transparent, having a haze value of less than about 55.

5. A method of preparing a dentifrice comprising the steps of:

a) preparing a premix, the premix containing no silica and having a refractive index of less than about 1.442; and
b) mixing the premix with an abrasive, precipitated silica, having;
   a refractive index of less than) about 1.4387;
   a light transmittance of greater than about 48%; and
   a Brass Einlehner abrasion value of greater than about 5 mg loss/100,000 rev., to form a dentifrice having an RDA of greater than about 50, a refractive index of less than about 1.442, and a haze value of less than about 70.

6. The method according to claim 5, wherein the dentifrice is transparent, having a haze value of less than about 70.

* * * * *

UNITED STATES PATENT AND TRADEMARK OFFICE
CERTIFICATE OF CORRECTION

PATENT NO.      : 6,616,916 B1
DATED           : September 9, 2003
INVENTOR(S)     : Karpe et al.

It is certified that error appears in the above-identified patent and that said Letters Patent is hereby corrected as shown below:

<u>Column 12,</u>
Line 57, "481%" should read -- 48% --.

Signed and Sealed this

Tenth Day of February, 2004

JON W. DUDAS
*Acting Director of the United States Patent and Trademark Office*